United States Patent [19]

Saleh et al.

[11] Patent Number: 5,561,094
[45] Date of Patent: Oct. 1, 1996

[54] DIALKYL ISOCYANATO TIN ALCOHOLATE CATALYSTS AND DIMERS THEREOF

[76] Inventors: Ramzi Y. Saleh, 13 Fir Ct., Flemington, N.J. 08822; Robert C. Michaelson, 1 Glendale Ter., Kinnelon, N.J. 07405; Elena N. Suciu, 417 Prospect St., Ridgewood, N.J. 07452; Barbara Kuhlmann, 1297 El Camino Village Dr., Houston, Tex. 77058

[21] Appl. No.: 429,057

[22] Filed: Apr. 26, 1995

Related U.S. Application Data

[62] Division of Ser. No. 170,468, Dec. 20, 1993.

[51] Int. Cl.⁶ ............................................. B01J 31/18
[52] U.S. Cl. .......................... 502/152; 502/155; 502/161; 502/167; 502/171; 556/32; 556/83
[58] Field of Search ..................... 502/152, 155, 502/161, 167, 171; 556/32, 83, 88, 107

[56] References Cited

U.S. PATENT DOCUMENTS

| | | | |
|---|---|---|---|
| 2,834,799 | 5/1958 | Sowa | 260/463 |
| 3,311,647 | 3/1967 | Stamm | 260/429.7 |
| 3,417,115 | 12/1968 | Stamm | 260/429.7 |
| 3,470,221 | 9/1969 | Rajendra et al. | 260/429.7 |
| 3,621,083 | 11/1971 | Price | 260/968 |
| 3,730,953 | 5/1973 | Naito et al. | 260/77.5 AM |
| 4,327,035 | 4/1982 | Heitz et al. | 260/463 |
| 4,331,610 | 5/1982 | Heitz et al. | 260/463 |
| 4,436,668 | 3/1984 | Harder et al. | 260/463 |
| 5,001,252 | 3/1991 | Bhattacharya | 558/277 |
| 5,003,084 | 3/1991 | Su et al. | 549/230 |
| 5,103,065 | 4/1992 | Bertleff et al. | 568/300 |

FOREIGN PATENT DOCUMENTS

| | | | |
|---|---|---|---|
| 0057825 | 1/1982 | European Pat. Off. | C07D 323/00 |
| 0061672 | 8/1984 | European Pat. Off. | C07C 69/96 |

*Primary Examiner*—Shrive Beck
*Assistant Examiner*—Timothy H. Meeks

[57] ABSTRACT

A process for making a dialkyl carbonate which comprises reacting urea with a first alcohol in a carbamate reactor at a temperature and pressure sufficient to convert said urea to an alkyl carbamate; and reacting the alkyl carbamate with a second alcohol in the presence of a dialkyl isocyanato alkoxy tin catalyst or derivatives in a carbonate reactor at a temperature and pressure sufficient to convert the alkyl carbamate to a dialkyl carbonate, wherein the molar ratio of alkyl carbamate to second alcohol is in the range between about 2:1 to about 10:1 and wherein dialkyl carbonate is present within the carbonate reactor in an amount between about 1 to about 3 weight %, based on total alkyl carbamate and second alcohol content, and wherein the second alcohol is either the same as or different from the first alcohol or a mixture of alcohols.

4 Claims, 1 Drawing Sheet

FIG. 1

DIALKYL ISOCYANATO TIN ALCOHOLATE CATALYSTS AND DIMERS THEREOF

This is a division, of application Ser. No. 08/170,468, filed Dec. 20, 1993.

The present invention relates generally to a process for the manufacture of dialkyl carbonate from urea and alcohols.

BACKGROUND OF THE INVENTION

Dimethyl carbonate (DMC) is an important industrial chemical which is typically synthesized from either phosgenation of methanol, alcoholysis of cyclic alkylene carbonate, or oxidative carbonylation of alcohols.

Each of the aforementioned processes has either commercial or technical disadvantages which make it desirable in the industry to develop a new process which avoids such set backs. For example, the phosgenation is a complicated and expensive process, alcoholysis is operationally and economically unfavorable since the production of the dialkyl carbonate always entails the simultaneous production of a stoichiometric amount of glycol, and the oxidative carbonylation process requires expensive technology for handling carbon monoxide under pressure and the avoidance of flammable mixtures in the reactor.

European Patent Publication No. 0 061 672 (Bayer AG) discloses a process for the preparation of carbonate esters by reacting alcohol and urea in the presence of a catalyst such as dibutyltin oxide ($Bu_2SnO$). Although this process overcomes the commercial and technological disadvantages of the phosgenation, alcoholysis, or oxidative carbonylation processes discussed above, as well as excess alcohol which is both costly and a reaction inhibitor, it is only capable of yielding carbonates at a conversion rate approaching 90%.

It would be most desirable to develop a process which has conversion and selectivity approaching 100%. In order to accomplish such a high percent of conversion of urea to carbamate and carbamate to carbonate the present inventors have discovered that it is important that (1) the mole fraction of alcohol be kept very low to avoid costly separation problems in the recovery section, (2) the catalyst be introduced in large amounts to avoid the formation of an unwanted azeotrope since excess catalyst suppresses the volatility of the alcohol, and (3) the amount of carbonate in the reactor should be kept low such that the formation of N-alkyl by-products is substantially eliminated. To maintain a low level of alcohol during the synthesis of carbonate, the present inventors have developed a novel organotin catalyst, i.e., a dialkyl isocyanato alkoxy tin(IV) and its derivatives, which is capable of exchanging its alkoxy group with the $NH_2$ group of the alkyl carbamate. The ability of the catalyst to exchange its alkoxy group for the $NH_2$ group allows for the use of significantly lower levels of alcohol than conventional process such as that disclosed in European Patent Publication No. 0 061 672 which relies solely upon the excess alcohol for removal of the $NH_2$ group from the carbamate.

Since the process according to the present invention utilizes significantly less alcohol than earlier known processes, it greatly increases the rate of carbonate removal from the reactor via distillation without the need to distill and recycle huge quantities of unreacted alcohols. Larger quantities of alcohol cause the rate of carbonate synthesis to slow since the alcohol rather than the carbonate is refluxed out of the reactor vessel, whereby a high concentration of carbonate remains in the reactor which causes the formation of undesirable N-alkyl by-products.

The present invention also provides many additional advantages which shall become apparent as described below.

SUMMARY OF THE INVENTION

A process for making a dialkyl carbonate which comprises reacting urea with a first alcohol in a carbamate reactor at a temperature and pressure sufficient to convert the urea to an alkyl carbamate, and reacting the alkyl carbamate with a second alcohol in the presence of a dialkyl isocyanato alkoxy tin(IV) catalyst or derivative thereof in a carbonate reactor at a temperature and pressure sufficient to convert the alkyl carbamate to a dialkyl carbonate. The second alcohol can be either the same as or different from the first alcohol, or a blend of various alcohols.

Alternatively, the alkyl carbamate can be obtained from a separate source such that dialkyl carbonate can be prepared from a one step process which comprises reacting the alkyl carbamate with an alcohol in the presence of a dialkyl isocyanato alkoxy tin(IV) catalyst or derivative thereof in a carbonate reactor at a temperature and pressure sufficient to convert the alkyl carbamate to a dialkyl carbonate.

This process is preferably continuous wherein the alkyl carbamate and the alcohol are continuously fed into the carbonate reactor to replace the alcohol and the dialkyl carbonate which is preferably removed from the carbonate reactor.

It is also preferable that the catalyst be present within the carbonate reactor in an amount in the range between about 5 to about 50 weight % based on the entire reaction solution, more preferably between about 10 to about 25 weight %.

The alcohol is added to the carbonate reactor to maintain a concentration of alcohol in the reactor such that there are 2 to 10 moles, more preferably 3 to 5 moles, of carbamate per mole of alcohol in the reactor, i.e., about 10 to about 30 weight % based on total carbamate and alcohol content of the reactor solution.

Alkyl carbamate is present within the carbonate reaction in an amount between about 70 to about 90 weight % based on total carbamate and alcohol content of the reactor solution.

Dialkyl carbonate is removed from the carbonate reactor such that the dialkyl carbonate is present within the reactor in an amount between about 1 to about 3 weight % based on total carbamate and alcohol content of the reactor solution.

The temperature of the carbamate reactor is maintained in the range between about 120° C. to about 220° C., and the pressure is autogeneous, i.e., depends on the vapor pressure of the alcohol, carbamate and ammonia. Whereas the temperature of the carbonate reactor is maintained in the range between about 140° C. to about 220° C., and the pressure is also autogeneous.

Optionally, a portion of the reaction mixture which typically comprises alkyl carbamate, alkylated by-products, dialkyl carbonate, catalyst and alcohol is either continuously or periodically removed from the carbonate reactor and treated with additional alcohol in a secondary reaction vessel under temperatures and pressures which are capable of converting the N-alkyl by-products to dialkyl carbonate and alkyl amine.

The novel catalyst is preferably a dialkyl isocyanato alkoxy tin(IV). Although dimers of dialkyl isocyanato alkoxy tin are also suitable catalysts.

Alternatively, the dialkyl isocyanato alkoxy tin(IV) catalyst can be formed in-situ within the carbonate reactor by adding dialkyl dialkoxy tin to the alkyl carbamate under excess alkyl carbamate conditions. The dialkyl dialkoxy tin(IV) and methyl carbamate are preferably reacted at a temperature in the range between about 80° C. to about 110° C.

Other and further objects, advantages and features of the present invention will be understood by reference to the following specification in conjunction with the annexed drawings, wherein like parts have been given like numbers.

DESCRIPTION OF THE PREFERRED EMBODIMENTS

Dialkyl carbonate is prepared in a two step process. The first step involves the synthesis of alkyl carbamate from urea or the like and an alcohol as described by equation (1) below:

(urea)    (alkyl carbamate)

where R is any aliphatic, cycloaliphatic, araliphatic, arylcycloaliphatic, heterocyclic aliphatic, or non-aromatic heterocyclic monohydric group comprising from 1 to about 16 carbon atoms. Equation (1) involves the reaction of urea or the like with an alcohol (e.g., methanol) at temperatures and pressures such that the alcohol which contains the $NH_3$ (a reaction product) is allowed to flash off from the reactor and which is replaced with fresh alcohol to maintain a constant level in the reactor. Urea can also be added to the reactor for a continuous operation. In this case alkyl carbamate and alcohol/$NH_3$ are continuously flashed off from the reactor and replaced with urea and fresh alcohol. Under these conditions, the equilibrium in equation (1) above is shifted to the right.

In the second step the alkyl carbamate synthesized in the first step or obtained elsewhere is reacted with an alcohol (i.e., the alcohol may be either the same or different from the alcohol used in the carbamate synthesis step or a mixture of various alcohols) in the presence of a dialkyl isocyanato alkoxy tin(IV) catalyst as described in equation (2) below:

(alkyl carbamate)    (dialkyl carbonate)

where R and R' are any aliphatic, cycloaliphatic, araliphatic, arylcycloaliphatic, heterocyclic aliphatic, or non-aromatic heterocyclic monohydric group comprising from 1 to about 16 carbon atoms. The alcohol and the formed dialkyl carbonate are distilled from the reactor and the alkyl carbamate/alcohol solution is fed to replace that which is removed by distillation. Under these conditions, virtually no by-products (i.e., alkylation products of the starting material) are formed and alkyl carbamate is quantitatively converted to dialkyl carbonate.

The dialkyl isocyanato alkoxy tin(IV) catalyst is preferably formed via the reaction of dialkyl dialkoxy tin(IV) with alkyl carbamate.

To avoid the formation of N-alkyl by-products during the carbonate synthesis process the following critical operating parameters must be adhered to: (1) addition of catalyst in an amount in the range between about 5 to about 50 weight % based on the entire reaction solution (more preferably between about 10–25 weight %), (2) maintaining very low free alcohol concentration in the reaction solution of about 10 to about 30 weight % based on total carbamate and alcohol content of the reactor solution, (3) maintaining a carbamate concentration in the range between about 70–90 weight % based on total carbamate and alcohol content of the reactor solution, and (4) distilling off dialkyl carbonate product such that it has a concentration of between about 1 to about 3 weight % based on total carbamate and alcohol content of the reactor solution. The alkyl carbamate to alcohol molar ratio is preferably in the range between about 2:1 to about 10:1, more preferably between about 3:1 to about 5:1.

It is also desirable to maintain the temperature of the carbonate reactor in the range between about 140° C. to about 220°. The pressure of the reactor is autogeneous, i.e., the sum of the vapor pressure of the alcohol, ammonia and alkyl carbamate at the reaction temperature.

The reaction is preferably run as a continuous process wherein dialkyl carbonate is continuously distilled from the reactor together with excess alcohol thereby preventing the formation of N-alkyl by-products and thus allowing extremely high selectivity and conversion of carbamate to carbonate.

In order to further avoid the formation of N-alkyl alkyl carbamate and N-alkyl urea by-products, the synthesis process of the present invention can be modified by treating a slip stream of the main reactor (which contains N-alkyl alkyl carbamate and N-alkyl urea together with the organotin catalyst, dialkyl carbonate, alkyl carbamate and alcohol) with excess alcohol in a secondary reaction vessel under suitable temperatures and pressures. Since the catalyst is present in the secondary reaction vessel it will convert the N-alkyl carbamate and urea by-products to dialkyl carbonate and alkyl amine according to the following three equations using methanol and dimethyl carbonate as an example:

It is also likely that any part of the catalyst which became inactive with time on stream may be restored to its original active state. The methyl amine generated is purged and scrubbed or incinerated and the ammonia is recovered and sent back to the urea plant. The balance of the stream, which contains the dimethyl carbonate, methanol and catalyst, is recycled back to the reactor. At the end of the reaction, the catalyst (e.g., dibutyl isocyanato methoxy tin(IV)) can alternatively be converted by treatment with water to dibutyltin oxide ($Bu_2Sn=O$), which can be recycled as a catalyst precursor.

Alcohols which are suitable for use as the first and second alcohols in the two step carbonate synthesis process of the present invention include methanol, ethanol, n-propanol, isopropanol, n-butanol, isobutanol, sec-butanol, n-pentanol, 2-pentanol, 3-pentanol, isopentanol, n-octanol, cyclohexanol, n-dodecanol, isododecanol, etc. Alcohols such as 3-buten-1-ol, benzyl alcohol, tetrahydro naphthol, furfuryl alcohol are also suitable for use in this invention.

The process of this invention is most suitable for making symmetrical or unsymmetrical carbonates from alkyl alcohols, preferably primary or secondary alkyl alcohols of from 1 to 6 carbon atoms. It may, however, also be used to make symmetrical and unsymmetrical carbonates from cycloalkyl alcohols, tertiary alcohols, allyl alcohol, non-aromatic heterocyclic alcohols, heterocyclic or aromatic substituted alkyl or allyl alcohols. Aromatic alcohols, such as, phenol are not suitable as starting materials for the process of the present invention.

The term "urea" as used herein includes any urea, N-alkyl substituted urea, N,N-dialkyl ureas, N,N'-dialkyl ureas, trialkyl ureas and tetraalkyl ureas. The most preferred is urea.

The process of the present invention utilizes a unique catalyst in the synthesis of dialkyl carbonate from alkyl carbamate and alcohol. This catalyst is capable of exchanging alkoxy groups with the $NH_2$ groups of the carbamate, thus requiring much less free alcohol in the reaction. Free alcohol is undesirable since it boils out of the reactor, necessitating costly recycle of such a large alcohol stream. A decrease in the amount of alcohol in the carbonate reaction allows the carbonate to be boiled from the reactor more rapidly thus shifting the carbonate reaction to the right and speeding carbamate conversion. It is critical to maintain the concentration of carbonate in the reactor below about 3%, above which undesirable alkyl by-products begin to form. This unique catalyst is capable of exchanging its —OR' groups with —$NH_2$ groups bonded to the alkyl carbamate. Moreover, the free alcohol replaces the —OR' on the catalyst, thereby continuously reactivating the catalyst.

The catalyst is preferably an organotin compound comprising alkoxy and isocyano groups bound to the same tin atom. One preferred organotin catalyst is dialkyl isocyanato alkoxy tin(IV) (e.g., dibutyl isocyanato methoxy tin(IV)) having the general structure set forth below:

where $R_1$ is any alkyl or aryl group; and R' is any aliphatic, cycloaliphatic, araliphatic, arylcycloaliphatic, heterocyclic aliphatic, or non-aromatic heterocyclic monohydric group comprising from 1 to about 16 carbon atoms; provided that R' is the same as the R' attached to the hydroxy group of the alcohol which is to be reacted with the alkyl carbamate.

The catalyst may also include distannoxane dimers such as 1-alkoxy-3-(isocyanato)tetraalkyldistannoxane where $R_1$ is any alkyl or aryl group; and R' is any aliphatic, cycloaliphatic, araliphatic, arylcycloaliphatic, heterocyclic aliphatic, or non-aromatic heterocyclic monohydric group comprising from 1 to about 16 carbon atoms; provided that R' is the same as the R' attached to the hydroxy group of the alcohol which is to be reacted with the alkyl carbamate.

It is also possible according to this invention to prepare higher carbonates such as bis-(2-ethylhexyl)carbonate from methyl carbamate and 2-ethyl-1-hexanol. Mixed carbonates such as methylisopropyl carbonate can also be prepared by reacting methyl carbamate or isopropyl carbamate with a methanol/isopropanol mixture under autogeneous pressure. This process can be applied to other carbonates using the corresponding alcohol mixture and alkyl carbamate or urea.

EXAMPLE 1

Dibutyl isocyanato methoxy tin(IV) (i.e., compound (I) above) was synthesized in quantitative yields from stoichiometric quantities of dibutyl tin dimethoxide ($Bu_2Sn(OMe)_2$) and methyl carbamate in refluxing toluene with removal of methanol (MeOH) in accordance with the below general equation:

Methyl carbamate (1.90 grams, 25.30 mmol) was added to a solution of $Bu_2Sn(OMe)_2$ (7.40 grams, 25.10 mmol) in toluene (100 ml). The solution was then refluxed under nitrogen to remove methanol for 1 hours. The solution was concentrated in vacuum to dryness generating 7 grams (91% yield) of a pale yellow oily material which crystallized on standing.

The resulting pale yellow oily material exhibited the following analysis: NMR:$^{119}$Sn, solv. $C_6D_6$; δ-180 (external reference key Sn 0.0 ppm); $^{13}C$ Solv $C_6O_6$; δ128.10 (—N=C=O) [for similar compounds containing SnNCO, see: M. Ratier, D. Khatmi, *Synth. Comm.* 1 *g*, (11/12), 1929, (1989)], δ51.44 (—OMe), δ27.59 (—$CH_2CH_2$—Sn), δ26.93 (—$CH_2CH_2CH_2$—Sn), δ22.50 (—$CH_2$—Sn), δ13.86 (—$CH_3$) (ref. at 128.0 ppm, benzene). $^1H$:δ3.2 (—$OCH_3$), δ1.5 (—$CH_2CH_2$—Sn), δ1.2 (—$CH_2CH_2CH_2$—Sn), δ1.1 (—$CH_2$—Sn), δ0.8 (—$CH_3$), —$CH_3$ /—$OCH_3$=2/1 (ref. 7.2 ppm, chloroform). IR (nujol): 2206 $cm^{-1}$ (vs) (—N=C=O), [for similar compounds see *Gmelin: Handbook of Inorganic Chemistry, Tin Compounds*, Vol. 8, 162 (1981)], 1036 $cm^{-1}$ (s) (—$OCH_3$), 683 $cm^{-1}$ (m) (—$CH_2$—Sn), 619 $cm^{-1}$ (m)(SnO) and 503 $cm^{-1}$ (m)(SnC).

Recrystallization of the crude pale yellow oily material from hexane following toluene evaporation yielded dibutyl isocyanato methoxy tin(IV) (i.e., compound (I) above) as a white solid with a melting point of 103°–105° C. Elemental analysis of the recrystallized product was as follows: mol. wt. 306; calculated for $C_{10}H_{21}NO_2Sn$; C=39.26, H=6.92, N=4.58, O=10.46, Sn=38.79% found: C=38.55, H=6.58, N=4.31, Sn=38.99%.

EXAMPLE 2

1-methoxy-3(isocyanato)tetrabutyldistannoxane (II) was synthesized quantitatively in a two step process from dibutyltin oxide using dimethyl carbonate in accordance with the equations set forth below:

$MeOH + O=C(OMe)_2$

The 1,3-bis(dimethoxy)tetrabutyldistannoxane dimer was synthesized according to the literature (see A. G. Davies, D. C. Kleinschmidt, P. R. Palan, S. C. Vasishtha, *Journal of the Chemical Society*, (C) pg. 3972, 1971), by adding dibutyltin oxide (246 grams, 0.99 mol.) to a solution of dimethyl carbonate (91.00 grams, 1.01 mol.), methanol (3.15 grams, 0.1 mol.) in toluene (1100 ml). The reaction was performed in a 2000 ml flask provided with stirring, temperature control, and condenser connected through a cold trap to a wet testmeter. The solution was heated within 40 minutes to reflux by continuous monitoring of the evolution of carbon dioxide through the wet testmeter. All dibutyltin oxide dissolved within one hour. The reflux continued for 2 more hours (i.e., a total reaction time of 3 hours). During this time the theoretical amount of carbon dioxide (0.5 mole) which corresponds to half of the dimethyl carbonate consumed, was removed. The solution was cooled under nitrogen. The analysis of a solution aliquot by $^{119}$Sn NMR, IR and gas chromatography/mass spectroscopy, confirmed that tetrabutyl dimethoxydistannoxane was indeed formed. After replacing the condenser with a Dewar column (Length=18 cm) provided with a distillation head, which was connected to a 250 ml collecting flask, the reaction solution was heated to 110° C. Thereafter, a hot solution of methyl carbamate (75 grams, 1 mole, or 31.5 grams, 0.5 moles) in toluene (200 ml) was added dropwise over a period of one hour.

During this time a mixture containing methanol, dimethyl carbonate and toluene, (approximately 200 grams) was collected until the temperature at the distillation head reached 110° C. The reaction flask was evaporated to half and, after cooling, the excess of methyl carbamate was filtered under nitrogen. The clear solution was concentrated at 50°–60° C., and at a pressure of 300 mmHg, to remove the remaining toluene. 273 grams of 1-methoxy-3-(isocyanato)tetrabutyldistannoxane (II) was obtained with corresponded to a 98% yield of semisolid white material.

An analysis of the resulting product which crystallized on standing (mp 124°–128° C.) was as follows: NMR: $^{119}$Sn, solv. toluene: δ–166, δ–206, in a ratio of 1:1 with minor peaks at δ–148 and δ–165, (external ref. Me$_4$Sn at 0.0 ppm), $^{13}$C NMR, solv. COCl$_3$: δ128.8, δ128.0 and 126.15 (—N=C=O), δ50.65 (—MeO), δ27.35, 27.17 (—CH$_2$CH$_2$—Sn), δ27.01, δ26.75 (—CH$_2$CH$_2$CH$_2$—Sn), δ22.56, δ22.21 (—CH$_2$—Sn), δ13.51 (—CH$_3$). IR neat: 2204 cm$^{-1}$ (—N=C=C), 1059 cm$^{-1}$ (vs) (—OMe), 730 cm$^{-1}$ (—CH$_2$C), 695 cm$^{-1}$ (—CH$_2$Sn), 613—580 cm$^{-1}$ [δ as (SnO)+δ as (snC)].

Elemental analysis: mol wt.=1110 Calculated for: C$_{36}$.H$_{78}$.N$_2$.0$_6$.Sn$_4$:

C=38.90.H=7.03.N=2.52.0=8.65,Sn=42.90%

Found: C=38.94.H=7.02.N=2.57.O=7.22,Sn=40.75%

EXAMPLE 3

Dibutyl isocyanato methoxy tin (I) was reacted with excess methanol to yield methyl carbamate and the corresponding dibutyltin dimethoxide according to the following equation:

$Bu_2Sn(OR')_2 + NH_2COOR'$

Under the conditions described below the reaction of Example 1 have been reversed.

A solution prepared from dibutyl isocyanato methoxy tin (as prepared in Example 1 above) (0.28 grams, 0.90 mmol) in MeOH (1.40 grams, 43.75 mmol) was heated in a 10 ml at 175° C. for one hour. The solution analyzed by $^{13}$C NMR exhibited the following spectrum: (NH$_2$COOMe) δ159.58 (C=O), dibutyltin dimethoxide δ51.59 (—OMe), and Bu$_2$Sn—( δ27.66, 27.22, 20.35 and 13.35 as assigned for dibutyl isocyanato methoxy tin. (Benzene resonance at 128 ppm was used as the reference).

EXAMPLE 4

The reaction of dibutyl isocyanato methoxy tin (I) with excess benzyl alcohol at 175° C. for six hours gave benzyl carbamate, methyl benzyl carbonate, dibenzyl carbonate, ammonia, methanol and dibenzoxydibutyltin in accordance with the following equation:

$Bz = CH_2C_6H_5$

In this example, a solution of dibutyl isocyanato methoxy tin (I)(as prepared in Example 1) (0.42 grams, 1.37 mmol) in benzylalcohol (2.00 grams, 18.50 mmol) was heated under nitrogen at 175° C. for six hours. The formation of benzylcarbamate, methyl benzyl carbonate and dibenzyl carbonate was confirmed by $^{13}$C NMR, IR, GC and MS.

EXAMPLE 5

A solution prepared from crude 1-methoxy-3 -(isocyanato)tetrabutyldistannoxane (II) (as prepared in Example 2) (1.10 grams, 1 mmol) in benzyl alcohol (1.57 grams, 14.52 mmol) was heated at 175° C. under nitrogen for four hours. The reaction was monitored by ammonia evolution. The formation of benzyl carbamate, methyl benzyl carbonate, and dibenzyl carbonate was confirmed by $^{13}$C NMR, IR, GC and mass spectroscopy (MS).

A comparative example was run wherein bis-(2-ethylhexyl)-carbonate was synthesized from methyl carbamate and 2-ethyl-1-hexanol under batch conditions. The reaction consisted of two steps: transesterification with formation of 2-ethylhexyl-carbamate and elimination of methanol, followed by carbonate formation with elimination of ammonia:

Catalysts (I) and (II) have been evaluated at different concentrations. Among other tin catalysts evaluated were also: 1,3 bis(isocyanato) tetrabutyl distannoxane (III), dibutyltin oxide (V), dibutyltin dimethoxide (IV), tetrabutyldimethoxydistannoxane (VI), and two thioisocyanato tin compounds, i.e., 1-methoxy-3-(isothiocyanato) tetrabutyldistannoxane (VII) and 1-hydroxy-3-(isothiocyanato) tetrabutyldistannoxane (VIII). The reactions were run at a temperature of between 190°–195° C. and pressure of 1 atm for approximately 12 hours. The conversion was calculated based on ammonia release. The selectivity by gas chromatography and $^{13}C$ NMR was 100%.

EXAMPLE 6

A solution prepared from the 1-methoxy-3-(isocyanato)tetrabutyldistannoxane dimer (II) (as described in Example 2 above) (3 grams, 10.80 meq Sn) (2.6 wt. %), 2-ethyl-1-hexanol (95 grams, 0.73 moles), and methyl carbamate (18.20 grams, 0.24 moles), was heated to 190° C. within 30–45 minutes, with stirring under nitrogen. During this period the methanol resulting from the transesterification reaction was collected in a Dean Stark trap. The gases containing ammonia were passed through a condenser to a sulfuric acid (1.6N) trap. After the collection of methanol, the Dean Stark trap was disconnected, the reaction flask was connected directly to the condenser, and the temperature was maintained at 190°–195° C. for 12 hours. Samples were taken periodically from the sulfuric acid trap and analyzed by potentiometric titration. The conversion of methyl carbamate and 2-ethyl-1-hexanol to dimethyl carbonate was 92%.

EXAMPLE 7

Same as Example 6 above, except that the 1-methoxy-3-(isocyanato) tetrabutyldistannoxane dimer (III) catalyst was added in an amount of 3 grams (10.80 meq Sn). The conversion of methyl carbamate and 2-ethyl-1-hexanol to dimethyl carbonate was 89%.

EXAMPLE 8

Same as Example 6 above, except that the catalyst was changed to $Bu_2Sn(OMe)_2$ (3 grams, 10 meq Sn) (2.6 wt. %). The conversion of methyl carbamate and 2-ethyl-1-hexanol to dimethyl carbonate was 91%.

EXAMPLE 9

Same as Example 6 above, except that the catalyst was changed to $Bu_2Sn=O$ (3 grams, 12 meq Sn) (2.6 wt. %). The conversion of methyl carbamate and 2-ethyl-1-hexanol to dimethyl carbonate was 80%.

EXAMPLE 10

Same as Example 6 above, except that the catalyst was changed to tetrabutyldimethoxydistannoxane dimer (described in Example 2) (3 grams, 11 meq Sn) (2.6 wt. %). The conversion of methyl carbamate and 2-ethyl-1-hexanol to dimethyl carbonate was 81%.

EXAMPLE 11

Same as example 10, except that the catalyst was changed to 2.6 wt. % tetrabutyldimethoxydistannoxane (VI) (3 grams, 11.00 meq Sn). The conversion of methyl carbamate and 2-ethyl-hexanol to dimethyl carbonate was 82%.

EXAMPLE 12

Same as example 7, except that the catalyst was changed to 1.3 wt. % 1,3-bis(isocyanato) tetrabutyl distannoxane (III) (1.5 grams, 5.40 meq Sn). The conversion of methyl carbamate and 2-ethyl-hexanol to dimethyl carbonate was 92%.

EXAMPLE 13

Same as example 8, except that the catalyst was changed to 1.3 wt. % dibutyltin dimethoxide (IV) (1.5 grams, 5.00 meq Sn). The conversion of methyl carbamate and 2-ethyl-hexanol to dimethyl carbonate was 91%.

EXAMPLE 14

Same as example 9, except that the catalyst was changed to 1.3 wt. % dibutyltin oxide (V) (1.5 grams, 6.00 meq Sn). The conversion of methyl carbamate and 2-ethyl-hexanol to dimethyl carbonate was 82%.

EXAMPLE 15

Same as example 10, except that the catalyst was changed to 1.5 wt. % tetrabutyldimethoxydistannoxane (VI) (1.5 grams, 5.5 meq Sn). The conversion of methyl carbamate and 2-ethyl-hexanol to dimethyl carbonate was 81%.

EXAMPLE 16

Same as example 6, except that the catalyst was changed to 1.3 wt. % dibutyl isocyanato methoxy tin (I) (1.5 grams, 5.00 meq Sn). The conversion of methyl carbamate and 2-ethyl-hexanol to dimethyl carbonate was 84%.

EXAMPLE 17

Same as example 6, except that the catalyst was changed to 1.3 wt. % 1,3-bis(isocyanato) tetrabutyl distannoxane (III) (1.5 grams, 5.5 meq Sn). The conversion of methyl carbamate and 2-ethyl-hexanol to dimethyl carbonate was 84%.

EXAMPLE 18

Same as example 6, except that the catalyst was changed to 1.3 wt. % 1-methoxy-3-(isothiocyanato) tetrabutyl distannoxane (VII) (1.5 grams, 5.25 meq Sn). The conversion of methyl carbamate and 2-ethyl-hexanol to dimethyl carbonate was 78%.

EXAMPLE 19

Same as example 6, except that the catalyst was changed to 1.3 wt. % 1-hydroxy-3-(isothiocyanato) tetrabutyl distannoxane dimer (VIII) (1.5 grams, 5.4 meq Sn). The conversion of methyl carbamate and 2-ethyl-hexanol to dimethyl carbonate was 65% with decomposition of the catalyst.

EXAMPLE 20

Same as example 6, except that the catalyst was changed to 0.6 wt. % 1,3-bis(isocyanato) tetrabutyl distannoxane (III) (0.7 grams, 2.50 meq Sn). The conversion of methyl carbamate and 2-ethyl-hexanol to dimethyl carbonate was 81%.

EXAMPLE 21

Same as example 6, except that the catalyst was changed to 0.6 wt. % dibutyltin dimethoxide (IV) (0.7 grams, 2.34 meq Sn). The conversion of methyl carbamate and 2-ethyl-hexanol to dimethyl carbonate was 77%.

EXAMPLE 22

Same as example 6, except that the catalyst was changed to 0.6 wt. % dibutyltin oxide (V) (0.7 grams, 2.40 meq Sn). The conversion of methyl carbamate and 2-ethyl-hexanol to dimethyl carbonate was 61%.

EXAMPLE 23

Same as example 6, except that the catalyst was changed to dibutyl isocyanato methoxy tin (I) (0.7 grams, 2.30 meq Sn). The conversion of methyl carbamate and 2-ethyl-hexanol to dimethyl carbonate was 73%.

EXAMPLE 24

A catalyst was recovered by treatment of 3 grams of the reaction product of example 6 with 2 grams of water while stirring. The resulting $Bu_2Sn=O$ was identified by IR.

EXAMPLE 25

(Comparative Example)

Figure 1:
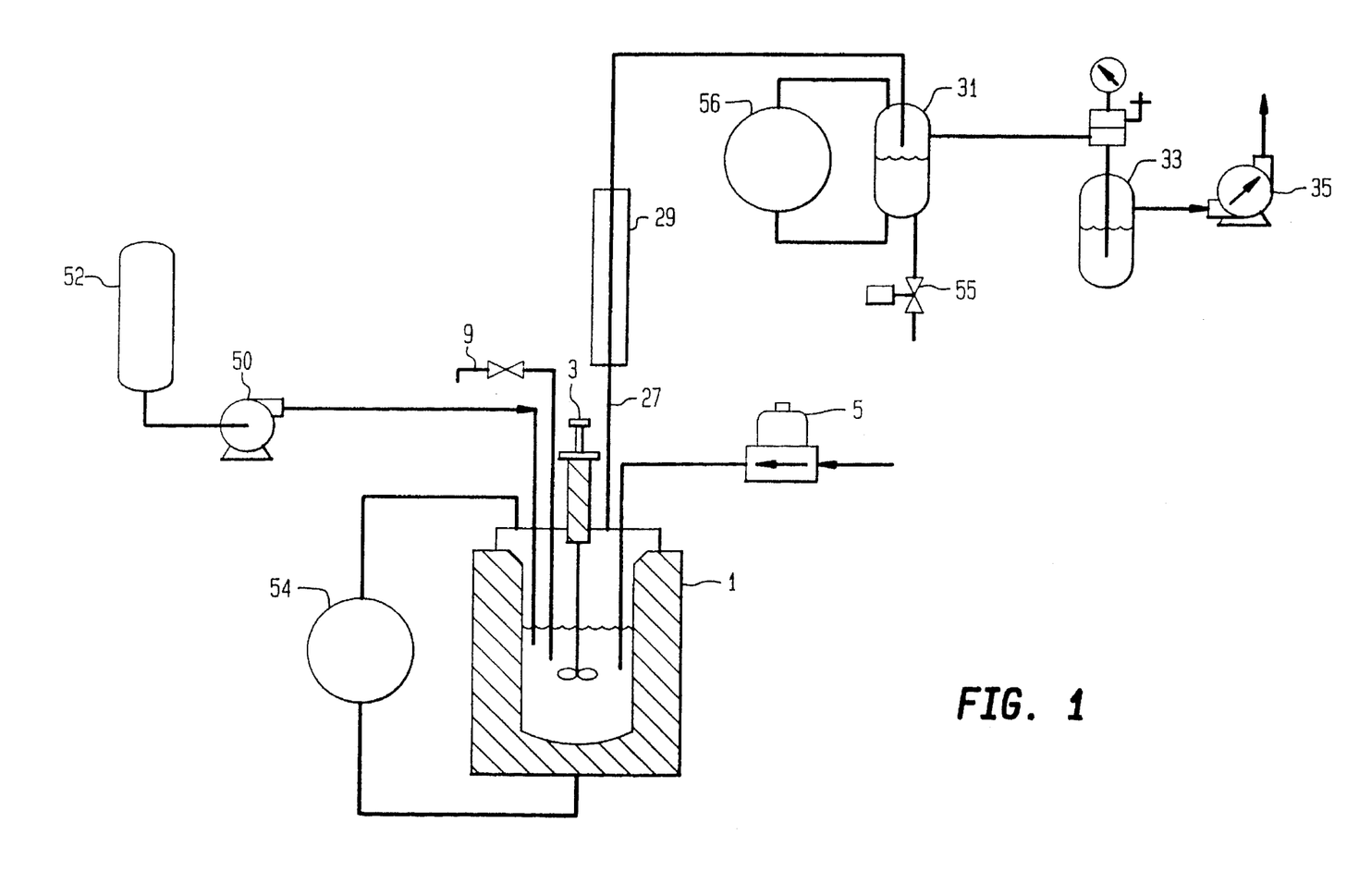
FIG. 1 is a schematic representation of a carbonate reactor without the recycle conduit or secondary reaction vessel in accordance with one embodiment of the present invention.

A mixture containing 125 grams of methyl carbamate (MC), 475 grams of methanol (MeOH) and 12.5 grams of dibutyltin oxide was added to a one liter stirred autoclave 1 shown in FIG. 1, attached hereto. Autoclave 1 is equipped with a sampling line 9, a feed system, a back pressure regulator 5 and an overhead condenser/collection system. The liquid level in autoclave 1 is maintained using a control device that activates the feed pump 50 when the liquid reaches a level below the set point. This device is used only for semi-continuous and continuous operations.

The feed system consists of a 20 liter feed tank 52 and a pump 50 which is activated by the level control device 54. Feed tank 52 is either charged with alcohol for semi-continuous operations or alcohol/methyl carbamate solutions for continuous operations. The overhead section comprises overhead conduit 27, a condenser 29, a knock-out (K-O) collection vessel 31 kept at approximately 0° C., a scrubber 33 filled with an aqueous solution of boric acid and a wet test meter 35. The liquid in collection vessel 31 is periodically drained via valve 55, weighed and analyzed. Drainage is activated by a level control device 56 connected to collection vessel 31. A mass flow controller 5 is used to purge and/or pressurize the system with nitrogen.

Autoclave 1 was pressurized with nitrogen at 613 psig ($4,227 \times 10^6$ $N/m^2$), then heated to 200° C. Stirrer 3 was set at 1000 rpm and a continuous flow of nitrogen at 50 cc/minute was maintained during the experiment. Under these conditions no liquid was allowed to evaporate and condense in the collection vessel 31 (i.e., it was a batch operation).

Small samples (approximately 1 ml each) were withdrawn from autoclave 1 and analyzed by gas chromatography (GS), for methyl carbamate (MC), dimethyl carbonate (DMC), N-methyl methyl carbamate (N-MMC) and methanol. The percent of methyl carbamate which was converted during this experiment was calculated according to the following formula:

$$\% \, MC \, \text{Convert} = \frac{(\text{grams } MC \text{ Converted})}{(\text{grams } MC \text{ Starting})} \times 100$$

The data are represented in Table 1 below. The results show poor rates and low yields of DMC and high levels of N-MMC.

TABLE 1

| Time | Autoclave, Wt. % | | | % MC |
|---|---|---|---|---|
| Hours | MC | DMC | N-MMC | Converted |
| 2 | 19.5 | 2.7 | 0 | 6.5 |
| 4 | 15.5 | 8.5 | 8.8 | 24.3 |
| 6 | 12.7 | 7.9 | 16.7 | 39.2 |
| 7 | 10.5 | 5.6 | 26.5 | 49.5 |

EXAMPLE 16

(Comparative Batch Operation)

This is a duplicate of Example 8 above, except that 15 grams of dibutyltin dimethoxide was used in place of dibutyltin oxide. Also, the autoclave was operated at 192° C. and 480 psig ($3.31 \times 10^6$ $N/m^2$). The results are tabulated in Table 2 below.

TABLE 2

| Time | Autoclave, Wt. % | | | % MC |
|---|---|---|---|---|
| Hours | MC | DMC | N-MMC | Converted |
| 3.5 | 13.8 | 5.9 | 2.5 | 33 |
| 5.75 | 10.8 | 6.4 | 6.7 | 48 |
| 7.25 | 9.2 | 5.8 | 10.6 | 56 |

As in Example 8, the rate is poor and the N-MMC level is high which caused the decline of DMC synthesis in the autoclave.

EXAMPLE 27

A solution comprising 158 grams of methyl carbamate, 532 grams of methanol and 17 grams of dibutyltin oxide was charged into an autoclave. The remainder of the procedure is similar to that set forth in Example 8 above, except that the temperature and pressure were 169° C. and 265 psig ($1.827 \times 10^6$ $N/m^2$), respectively, and the experiment was performed in a semi-continuous mode in which the 20 liter feed tank was charged with methanol. This methanol was continuously added to the autoclave to replace that accumulated in the collection vessel in the overhead section of the system. The collection vessel was drained periodically and the liquid collected was analyzed by GC. The nitrogen purge through the autoclave was set at 100 cc/minute. Autoclave sample analyses are summarized in Table 3 below.

TABLE 3

| Time | Autoclave, Wt. % | | | % MC |
|---|---|---|---|---|
| Hours | MC | DMC | N-MMC | Converted |
| 0.5 | 19.23 | 0 | 0 | 1.3 |
| 1.5 | 20.55 | 0.2 | 0 | 2.2 |
| 2 | 20.66 | 0.34 | 0 | 1.5 |
| 2.5 | 20.04 | 0.49 | 0 | 17.3 |
| 3.25 | 19.13 | 0.63 | 0 | 17.4 |
| 3.75 | 19.39 | 0.66 | 0 | 16.6 |
| 4.75 | 18.15 | 0.71 | 0 | 23.7 |
| 6 | 17.7 | 0.69 | 0 | 26.1 |
| 7 | 16.1 | 0.68 | 0 | 31.1 |
| 8 | 15.62 | 0.67 | 0 | 34.9 |

As demonstrated in Table 3, only DMC was formed (i.e., no N-MMC was observed). The samples recovered from the collection vessel also exhibited only DMC and methanol. These results demonstrate that maintaining low levels of DMC in the reactor produces no undesirable N-methyl methyl carbamate by-product and essentially 100% selectivity to DMC.

EXAMPLE 28

This is a repeat of Example 27 above, except that 34 grams of dibutyltin dimethoxide (which converts to dibutyl isocyanato methoxy tin(IV) via reaction with methyl carbamate) was used as the catalyst. The results are summarized in Tables 4 (autoclave samples) and 5 (collection vessel samples) below.

TABLE 4

| Time | Autoclave, Wt. % | | | % MC |
|---|---|---|---|---|
| Hours | MC | DMC | N-MMC | Converted |
| 1 | 19.07 | 0.27 | 0 | 16.3 |
| 2 | 17.56 | 0.73 | 0 | 24.2 |
| 3 | 16.27 | 1.18 | 0 | 29.6 |
| 3.6 | 15.96 | 1.44 | 0 | 31.5 |
| 4 | 15 | 1.65 | 0 | 35 |
| 4.5 | 14.49 | 1.81 | 0 | 38.2 |
| 5 | 13.88 | 2.03 | 0 | 41 |
| 5.5 | 13.23 | 2.08 | 0 | 43.6 |
| 6.16 | 12.56 | 2.34 | 0 | 46.6 |
| 6.83 | 12.49 | 2.44 | 0 | 46.7 |
| 7.17 | 11.66 | 2.51 | 0 | 50.2 |
| 7.66 | 11.08 | 2.49 | 0 | 52.5 |
| 8.16 | 11.00 | 2.50 | 0 | 52.6 |

TABLE 5

| Time Hours | Wt. % DMC in Overhead |
|---|---|
| 2.33 | 0.64 |
| 3.33 | 0.98 |
| 4.33 | 1.3 |
| 5.33 | 1.59 |
| 6.33 | 1.72 |
| 7.33 | 1.92 |
| 8.16 | 2.1 |

As in Example 27 above, no N-methyl methyl carbamate by-product was formed. The lack of N-methyl methyl carbamate formation is due to maintaining the DMC level in the autoclave at a relatively low level. Likewise, no N-methyl methyl carbamate was detected in the overhead stream.

EXAMPLE 29

A mixture containing 257 grams of methyl carbamate, 429 grams of methanol and 120 grams of dibutyltin dimethoxide (which converts to dibutyl isocyanato methoxy tin(IV) via reaction with methyl carbamate) was charged into an autoclave. The autoclave was pressurized at 242 psig ($1.669 \times 10^6$ N/m$^2$) then heated to 168° C. A 20 liter feed tank was charged with methanol. Analyses of autoclave and overhead samples are summarized in Tables 6 and 7, respectively.

TABLE 6

| Time | Autoclave, Wt. % | | | | % MC |
|---|---|---|---|---|---|
| Hours | MC | DMC | N-MMC | MU | Converted |
| 0.75 | 29.9 | 0.75 | 0 | 0 | 37.9 |
| 1.17 | 28.3 | 1.61 | 0 | 0 | 43.4 |
| 1.91 | 19.02 | 2.95 | 0 | 0.53 | 64.1 |
| 2.49 | 13.3 | 4.08 | 0 | 0.60 | 76.1 |
| 2.91 | 11.7 | 4.60 | 0.11 | 0.59 | 82.2 |
| 4.08 | 10.1 | 5.2 | 0.23 | 0.69 | 83.0 |
| 5.25 | 9.5 | 5.7 | 0.30 | 0.73 | 83.5 |
| 6 | 7.8 | 5.4 | 0.34 | 0.74 | 85.7 |
| 6.67 | 5.9 | 5.3 | 0.27 | 0.57 | 90.3 |
| 7.34 | 4.7 | 5.4 | 0.41 | 0.81 | 92.3 |
| 8.25 | 3.8 | 5.1 | 0.47 | 0.81 | 94.0 |

* MU denotes methyl urea.

TABLE 7

| Time Hours | Wt. % DMC in Overhead |
|---|---|
| 0.42 | 1.36 |
| 2.17 | 2.29 |
| 3.42 | 3.31 |
| 4.58 | 3.87 |
| 5.25 | 4.04 |
| 6.17 | 4.05 |
| 6.92 | 4.02 |
| 7.54 | 4.08 |

This example shows high reaction rates as a result of ammonia removal from the autoclave and high level of catalyst. The methyl carbamate was essentially converted to DMC with less than 1% of N-MMC and methyl urea (MU) by-products being formed.

EXAMPLE 30

This is a repeat of Example 29 above, except that the autoclave was operated continuously by charging the feed tank with a solution of 15.27 wt. % methyl carbamate and 84.73 wt. % methanol. Also, the autoclave was set at 174° C. and 151 psig ($1.041 \times 10^6$ N/m$^2$). The results are summarized in Tables 8 and 9 below.

TABLE 8

| Time | Autoclave, Wt. % | | | MC:MeOH |
|---|---|---|---|---|
| Hours | MC | DMC | N-MMC | (molar) |
| 0.17 | 52.31 | 0.26 | 0 | 0.501 |
| 0.33 | 54.37 | 0.28 | 0 | 0.511 |
| 0.58 | 55.68 | 0.35 | 0 | 0.540 |
| 1 | 54.72 | 1.10 | 0 | 0.529 |
| 1.67 | 56.91 | 3.24 | 0 | 0.560 |

TABLE 8-continued

| Time | Autoclave, Wt. % | | | MC:MeOH |
|---|---|---|---|---|
| Hours | MC | DMC | N-MMC | (molar) |
| 2.83 | 56.11 | 5.03 | 0 | 0.616 |
| 5 | 58.67 | 6.28 | 0.47 | 0.724 |
| 6.08 | 57.42 | 7.88 | 1.32 | 0.734 |
| 7.33 | 56.84 | 7.81 | 2.03 | 0.728 |
| 9 | 56.44 | 7.88 | 2.48 | 0.725 |
| 11 | 56.27 | 7.57 | 2.93 | 0.722 |
| 13 | 55.97 | 7.40 | 3.63 | 0.724 |
| 15 | 53.5 | 7.56 | 4.72 | 0.667 |
| 17 | 53.71 | 7.58 | 5.28 | 0.685 |
| 19 | 53.13 | 7.42 | 5.90 | 0.676 |
| 21 | 51.96 | 7.30 | 6.59 | 0.649 |
| 24 | 47.23 | 6.92 | 7.67 | 0.528 |
| 26 | 45.59 | 6.72 | 8.50 | 0.496 |
| 28.83 | 50.64 | 7.37 | 8.48 | 0.626 |
| 30.42 | 51.44 | 7.61 | 8.95 | 0.669 |
| 31.34 | 50.79 | 7.16 | 8.80 | 0.652 |

TABLE 9

| Time Hours | Wt. % DMC in Overhead |
|---|---|
| 1.08 | 3.39 |
| 2 | 7.54 |
| 2.83 | 9.51 |
| 5.17 | 13.08 |
| 7 | 14.18 |
| 8.75 | 14.25 |
| 10.75 | 14.63 |
| 12.75 | 13.68 |
| 14.75 | 16.16 |
| 16.75 | 13.12 |
| 18.75 | 14.63 |
| 20.75 | 14.92 |
| 22.75 | 11.54 |
| 24.75 | 11.12 |
| 26.75 | 11.77 |
| 29 | 13.57 |
| 30.5 | 16.82 |
| 31.5 | 15 |

This example demonstrates that essentially 100% conversion of methyl carbamate can be achieved when methyl carbamate is continuously charged to the reactor. This conversion is based on the fact that the average methyl carbamate to methanol molar ratio in the autoclave stayed at 0.63±0.08 throughout the experiment. The autoclave data, however, show a rapid increase in N-MMC with time on stream, and a relatively constant level of DMC at about 7 to about 8 wt. %. No N-MMC was observed in the overhead stream.

EXAMPLE 31

This is a repeat of Example 30, except that the feed tank was charged with a solution of 8.27 wt. % methyl carbamate and 91.73 wt. % methanol. Also, the autoclave was operated at 164° C. and 155 psig (1.069×10$^6$ N/m$^2$). The results are summarized in Tables 10 and 11.

TABLE 10

| Time | Autoclave, Wt. % | | | MC:MeOH |
|---|---|---|---|---|
| Hours | MC | DMC | N-MMC | (molar) |
| 0.25 | 53.4 | 0 | 0 | 0.49 |
| 0.38 | 54.27 | 0 | 0 | 0.51 |
| 0.58 | 53.49 | 0 | 0 | 0.49 |
| 0.75 | 51.1 | 1.18 | 0 | 0.46 |
| 1.5 | 52.13 | 3.52 | 0 | 0.46 |
| 3 | 47.64 | 7.03 | 0 | 0.45 |
| 5 | 45.84 | 8.22 | 0.31 | 0.43 |
| 6 | 45.42 | 8.84 | 0.43 | 0.43 |
| 7 | 44.45 | 9.1 | 0.56 | 0.41 |
| 8.5 | 44.48 | 9.17 | 0.6 | 0.42 |
| 9.5 | 44.36 | 9.04 | 0.69 | 0.41 |
| 11 | 43.6 | 8.81 | 0.8 | 0.4 |
| 12.5 | 43.05 | 8.81 | 0.88 | 0.39 |
| 14 | 42.18 | 8.51 | 1 | 0.37 |
| 15.5 | 41.67 | 8.45 | 1.11 | 0.36 |
| 17 | 42.29 | 8.3 | 1.16 | 0.37 |
| 18.5 | 41.43 | 8.12 | 1.23 | 0.36 |
| 20 | 40.99 | 8.07 | 1.34 | 0.35 |
| 21.5 | 40.43 | 7.94 | 1.56 | 0.34 |
| 23 | 40.83 | 7.86 | 1.5 | 0.35 |
| 24 | 39.77 | 7.67 | 1.54 | 0.33 |
| 25.17 | 39.23 | 7.84 | 1.62 | 0.33 |
| 27 | 39.7 | 8.12 | 1.78 | 0.32 |

TABLE 11

| Time Hours | Wt. % DMC in Overhead |
|---|---|
| 1 | 3.36 |
| 2 | 5.33 |
| 3 | 7.49 |
| 4.92 | 9.52 |
| 5.92 | 9.75 |
| 7 | 10.28 |
| 8.5 | 10.25 |
| 9.58 | 9.83 |
| 11.5 | 10.21 |
| 13 | 10.03 |
| 14.5 | 9.31 |
| 16 | 9.63 |
| 17.5 | 9.25 |
| 19 | 8.63 |
| 20.5 | 8.82 |
| 22 | 8.59 |
| 23.5 | 8.23 |
| 24.42 | 8.36 |
| 25.5 | 8.01 |

As in Example 30, the methyl carbamate conversion is essentially 100% as evidenced by the constant methyl carbamate to methanol molar ratio in the autoclave. The percent N-MMC, however, is significantly lower than that observed in Example 30 due primarily to the lower operating temperature and faster rate of removing DMC from the reactor. The overhead samples contained only DMC and methanol (i.e., no N-MMC).

EXAMPLE 32

This is a repeat of Example 31, except that the autoclave was operated at 160° C. and 102 psig (7.033×10$^5$ N/m$^2$). The data is shown in Tables 12 and 13.

TABLE 12

| Time | Autoclave, Wt. % | | | MC:MeOH |
|---|---|---|---|---|
| Hours | MC | DMC | N-MMC | (molar) |
| 0.17 | 59.01 | 0 | 0 | 0.61 |

TABLE 12-continued

| Time | Autoclave, Wt. % | | | MC:MeOH |
|---|---|---|---|---|
| Hours | MC | DMC | N-MMC | (molar) |
| 0.33 | 52.75 | 0.34 | 0 | 0.48 |
| 0.58 | 54.69 | 0.41 | 0 | 0.52 |
| 1.5 | 58.23 | 0.8 | 0 | 0.61 |
| 2.67 | 62.66 | 1.49 | 0 | 0.75 |
| 4.83 | 66.04 | 1.6 | 0 | 0.87 |
| 7 | 63.72 | 2.16 | 0 | 0.8 |
| 9 | 67.78 | 2.23 | 0 | 0.96 |
| 10.5 | 69.83 | 1.88 | 0 | 1.05 |
| 14.5 | 65.56 | 2.29 | 0 | 0.97 |
| 17 | 68.78 | 1.95 | 0 | 1 |
| 20 | 68.55 | 2.21 | 0 | 1 |
| 23 | 68.39 | 2.2 | 0 | 0.99 |
| 26.08 | 64.4 | 2.52 | 0 | 0.99 |
| 27.08 | 68.42 | 2.2 | 0 | 0.99 |
| 30.33 | 68.55 | 2.14 | 0 | 1 |
| 33.33 | 69.13 | 2.1 | 0 | 1.03 |
| 36.5 | 69.1 | 1.99 | 0 | 1.02 |
| 40 | 65 | 2.82 | 0 | 0.99 |
| 44 | 68.1 | 2.52 | 0 | 1 |
| 47 | 68.41 | 2.29 | 0 | 1 |
| 50 | 69.2 | 2.43 | 0 | 1.05 |
| 53 | 68.68 | 2.28 | 0 | 1.02 |
| 56 | 67.14 | 2.68 | 0 | 0.96 |
| 60 | 69.49 | 2.18 | 0 | 1.06 |
| 64 | 70.24 | 2.2 | 0 | 1.1 |
| 68 | 69.13 | 2.49 | 0 | 1.05 |
| 72 | 69.42 | 2.35 | 0 | 1.04 |
| 75 | 69.18 | 2.41 | 0 | 1.05 |
| 78.08 | 68.72 | 2.27 | 0 | 1.03 |
| 81.08 | 70.05 | 2.13 | 0 | 1.09 |

TABLE 13

| Time Hours | Wt. % DMC in Overhead |
|---|---|
| 1 | 1.47 |
| 1.92 | 2.18 |
| 2.75 | 3.05 |
| 5.33 | 3.71 |
| 7.58 | 4.04 |
| 9.08 | 3.68 |
| 10.58 | 2.82 |
| 14.58 | 3.1 |
| 17.08 | 3.42 |
| 20.08 | 4.39 |
| 23.08 | 3.39 |
| 26.17 | 3.31 |
| 29.33 | 3.07 |
| 32.67 | 3.28 |
| 36 | 3.29 |
| 39.5 | 3.41 |
| 43.83 | 3.44 |
| 46.83 | 3.49 |
| 50.08 | 3.58 |
| 53.08 | 3.55 |
| 56.08 | 3.68 |
| 60.08 | 3.77 |
| 64.08 | 3.71 |
| 68.08 | 3.76 |
| 72.08 | 3.83 |
| 75 | 3.85 |
| 78.2 | 3.85 |
| 81.17 | 3.7 |

As in Example 31, the methyl carbamate conversion was essentially 100% with a constant methyl carbamate to methanol molar ratio of approximately 1.0 in the autoclave. The significant finding from this example is that no N-MMC was detected either in the reactor or the overhead because the percent DMC in the reactor was kept at less than 3 wt. % and the lower operating temperature.

EXAMPLE 33

In this experiment, the procedures of Example 32 were repeated at 150° C. and 65 psig ($4.482 \times 10^5$ N/m$^2$). The results are represented in Tables 14 and 15.

TABLE 14

| Time | Autoclave, Wt. % | | | MC:MeOH |
|---|---|---|---|---|
| Hours | MC | DMC | N-MMC | (molar) |
| 0.28 | 42.56 | 0 | 0 | 0.32 |
| 1 | 54.07 | 0.61 | 0 | 0.51 |
| 2.25 | 68.46 | 0.77 | 0 | 0.95 |
| 5.83 | 71.12 | 1.26 | 0 | 1.1 |
| 12 | 72.67 | 1.35 | 0 | 1.19 |
| 18 | 73.02 | 1.51 | 0 | 1.2 |

TABLE 15

| Time Hours | Wt. % DMC in Overhead |
|---|---|
| 2.33 | 1.76 |
| 4.55 | 2.12 |
| 6.5 | 2.31 |
| 8.5 | 2.08 |
| 11.5 | 2.08 |
| 15 | 2.13 |
| 19 | 2.33 |

As demonstrated in Example 32, the formation of N-MMC can be minimized or avoided by maintaining a low level of DMC in the autoclave.

EXAMPLE 34

This is a repeat of Example 32, except that the autoclave was operated at 155° C. and 63 psig ($4.344 \times 10^5$ N/m$^2$) and the experiment was terminated after 249.5 hours. The feed tank was charged with a solution of 8.27 wt. % methyl carbamate and 91.73 wt. % methanol for the first 18 hours. The solution was then replaced with another solution containing 10.98 wt. % methyl carbamate and 89.02 wt. % methanol for the next 39 hours, and then a final solution of 9.63 wt. % methyl carbamate and 90.37 wt. % methanol was employed until the end of the experiment. Tables 16 and 17 represent a summary of the results.

TABLE 16

| Time | Autoclave, Wt. % | | | MC:MeOH |
|---|---|---|---|---|
| Hours | MC | DMC | N-MMC | (molar) |
| 0.58 | 50.44 | 1.3 | 0 | 0.45 |
| 1.25 | 58.55 | 1.88 | 0 | 0.63 |
| 2.5 | 65.19 | 1.76 | 0 | 0.84 |
| 4.75 | 73.06 | 2.13 | 0 | 1.26 |
| 8.5 | 74.47 | 1.31 | 0 | 1.31 |
| 12.75 | 74.74 | 1.11 | 0 | 1.32 |
| 15.75 | 75.39 | 1.04 | 0 | 1.36 |
| 18.75 | 76.12 | 1.11 | 0 | 1.43 |
| 21.75 | 76.59 | 0.87 | 0 | 1.45 |
| 25.25 | 76.47 | 1.02 | 0 | 1.45 |
| 28 | 77.24 | 0.91 | 0 | 1.51 |
| 30 | 77.58 | 1.01 | 0 | 1.54 |
| 32.5 | 78.58 | 1.22 | 0 | 1.66 |
| 33.25 | 77.61 | 1.52 | 0 | 1.59 |
| 37.75 | 79.01 | 1.05 | 0 | 1.69 |
| 41.75 | 76.66 | 0.99 | 0 | 1.59 |
| 45.75 | 81.92 | 0.95 | 0 | 2.03 |
| 47.75 | 85.7 | 1.07 | 0 | 2.76 |
| 52.33 | 87.67 | 1.23 | 0 | 3.4 |

TABLE 16-continued

| Time | Autoclave, Wt. % | | | MC:MeOH |
|---|---|---|---|---|
| Hours | MC | DMC | N-MMC | (molar) |
| 57 | 88.54 | 1.05 | 0 | 3.63 |
| 58.25 | 88.74 | 1.14 | 0 | 3.74 |
| 63.25 | 87.95 | 0.94 | 0.35 | 3.5 |
| 69.25 | 88.34 | 0.87 | 0.46 | 3.6 |
| 74.83 | 87.47 | 1.13 | 0.53 | 3.4 |
| 80 | 88.17 | 0.94 | 0.56 | 3.5 |
| 88 | 87.75 | 0.96 | 0.63 | 3.4 |
| 98.08 | 86.95 | 1.26 | 0.76 | 3.4 |
| 105 | 86.58 | 1.28 | 0.78 | 3.3 |
| 122.5 | 85.76 | 1.24 | 0.93 | 3.1 |
| 147.08 | 85.85 | 1.22 | 1.07 | 3.1 |
| 157.75 | 85.01 | 1.5 | 1.05 | 3 |
| 166.08 | 85.86 | 1.28 | 1.05 | 3.1 |
| 180 | 86.17 | 1.64 | 1.13 | 3.34 |
| 190.5 | 85.52 | 1.58 | 1.34 | 3.2 |
| 202.5 | 85.7 | 1.84 | 1.13 | 3.25 |
| 214.75 | 86.15 | 1.3 | 1.17 | 3.23 |
| 238.67 | 87.16 | 1.37 | 1.05 | 3.6 |
| 249.5 | 89.16 | 0.9 | 1.2 | 4.1 |

TABLE 17

| Time Hours | Wt. % DMC in Overhead |
|---|---|
| 1.33 | 3.02 |
| 2.67 | 3.95 |
| 6.75 | 6.29 |
| 8.75 | 2.95 |
| 13.25 | 2.68 |
| 15.5 | 2.85 |
| 17.75 | 2.98 |
| 20 | 3.33 |
| 22 | 3.4 |
| 24 | 3.45 |
| 26 | 3.39 |
| 29.5 | 3.6 |
| 32 | 4.49 |
| 38 | 2.56 |
| 40 | 2.71 |
| 42 | 2.79 |
| 44 | 2.91 |
| 47.25 | 3.35 |
| 50 | 4.06 |
| 57.33 | 7.74 |
| 69.33 | 7.34 |
| 75 | 7.44 |
| 88.25 | 7.3 |
| 98.17 | 8 |
| 105.42 | 8.7 |
| 122.75 | 9.53 |
| 151.75 | 9.74 |
| 166.42 | 9 |
| 180.5 | 8.77 |
| 190.92 | 9 |
| 203 | 8.57 |
| 214.75 | 8.62 |
| 238.25 | 8.6 |
| 249.75 | 8.45 |

This example illustrates that high ratios of methyl carbamate to methanol can be achieved without forming significant levels of N-MMC as long as the DMC content in the autoclave is kept low. This greatly increases the DMC concentration in the overhead, reducing the need for costly alcohol recycle.

EXAMPLE 35

At the end of Example 34, the solution in the feed tank was replaced with methanol and the experiment was continued for an additional 14.5 hours. The N-MMC in the autoclave was reduced from 1.2 wt. % to 0.26 wt. %. These results are potentially useful in developing a catalyst cycle for the process aimed at removing undesirable by-products when they accumulate in the reactor with time on stream. This can be accomplished by treating a slip stream of the reactor with pure methanol at the proper temperature and pressure. The treated stream is then fractionated to recover DMC and the methanol is mixed with fresh methyl carbamate and recycled back to the reactor.

EXAMPLE 36

A mixture containing 240 grams of urea and 384 grams of methanol was charged into an autoclave. The autoclave was pressurized at 193 psig ($1.331 \times 10^6$ N/m$^2$), using nitrogen, then heated to 160° C. The experiment was performed in a batch mode where no liquid accumulated in the collection vessel and no methanol was added to the autoclave during the experiment. Samples were withdrawn from the autoclave and analyzed for methyl carbamate and methanol. Percent conversion was calculated using the following formula:

$$\% \text{ Conversion} = \frac{(\text{Starting Moles Urea} - \text{Moles } MC)}{(\text{Starting Moles Urea})} \times 100$$

The results are summarized in Table 18 wherein a maximum conversion of only 62.5% was achieved after 6.5 hours.

TABLE 18

| Time | Autoclave | |
|---|---|---|
| Hours | % Conversion | Wt. % MC |
| 0.25 | 0 | 0 |
| 0.5 | 0 | 0 |
| 0.67 | 0 | 0 |
| 0.75 | 6.54 | 4.5 |
| 1.83 | 28.06 | 18.08 |
| 2.41 | 45.78 | 26.69 |
| 3.58 | 55.65 | 31.46 |
| 4.63 | 66.08 | 36.83 |
| 5.83 | 59.57 | 31.23 |
| 6.5 | 62.51 | 31.89 |
| 7.17 | 61.16 | 31.45 |

EXAMPLE 37

This is a repeat of Example 36, except that the autoclave was operated at 159° C. with a back pressure of 181 psig ($1,248 \times 10^6$ N/m$^2$). Under these conditions methanol was allowed to evaporate and condense in the collection vessel. The liquid level in the autoclave was kept constant by continuously pumping methanol placed in the 20 liter feed tank. Analysis of the autoclave samples is summarized in Table 19 below. The data show that 100% conversion to DMC is achieved after hours. The collection vessel samples showed only methanol. As such, this Example 24 demonstrates that removing methanol containing ammonia from the reactor and replacing it with fresh methanol results in faster rates and more efficient removal of ammonia from the reactor.

TABLE 19

| Time | Autoclave | |
|---|---|---|
| Hours | % Conversion | Wt. % MC |
| 0.5 | 5.61 | 3.41 |

TABLE 19-continued

| Time | Autoclave | |
|---|---|---|
| Hours | % Conversion | Wt. % MC |
| 0.75 | 15.4 | 9.73 |
| 1.5 | 34.7 | 20.55 |
| 2 | 48.5 | 27.81 |
| 2.58 | 61.1 | 32.81 |
| 3.5 | 82.5 | 41.97 |
| 4.5 | 82.2 | 39.84 |
| 5.5 | 87.1 | 41.44 |
| 6 | 93 | 44.71 |
| 7 | 100 | 47.3 |

EXAMPLE 38

This is a repeat of Example 37, except that 12 grams of dibutyltin dimethoxide were mixed with the urea/methanol mixture. The experiment was carried in a semi-continuous mode at the same temperature and back pressure used in Example 37. The results, summarized in Table 20, show slightly faster rates than observed in Example 37 when no catalyst was used. The collection vessel showed only methanol.

TABLE 20

| Time | Autoclave | |
|---|---|---|
| Hours | % Conversion | Wt. % MC |
| 0.33 | 0 | 0 |
| 0.58 | 32.1 | 20.07 |
| 0.75 | 40.7 | 25.05 |
| 1.25 | 55.2 | 31.1 |
| 1.92 | 64.5 | 33.34 |
| 2.25 | 72 | 35.66 |
| 3.25 | 88.2 | 43.24 |
| 4.25 | 92.5 | 43.82 |
| 5.38 | 90 | 40.05 |
| 6 | 94.6 | 44.96 |

The conclusion from Examples 36, 37 and 38 is that operating in a semi-continuous mode in which ammonia is continuously removed from the reactor is crucial in order to achieve complete conversion of the urea to methyl carbamate and that the use of catalyst is not essential in this step.

EXAMPLE 39

(Comparative)

A mixture containing 358 grams methyl carbamate, 287 grams of isopropanol (IPA) and 169 grams of dibutyltin dimethoxide was charged into an autoclave. The experiment was carried out in a semi-continuous mode in which the 20 liter feed tank was charged with IPA and the autoclave was set at 153° C. and 72 psig ($4.964 \times 10^5$ N/m$^2$) back pressure. Autoclave samples were analyzed by gas chromatography and the results are summarized in Table 21.

TABLE 21

| Time | Autoclave, Wt. % | | |
|---|---|---|---|
| Hours | MC | IPC | DIPC |
| 0.25 | 24.4 | 21 | 0 |
| 0.42 | 20.13 | 21.85 | 0 |
| 0.75 | 16.27 | 27.73 | 0 |

TABLE 21-continued

| Time | Autoclave, Wt. % | | |
|---|---|---|---|
| Hours | MC | IPC | DIPC |
| 1.25 | 9.13 | 35.6 | 0 |
| 2.08 | 1.02 | 38.15 | 1.68 |
| 3.25 | 0 | 41.7 | 2.89 |
| 4.42 | 0 | 38.83 | 3.63 |
| 5.5 | 0 | 36.98 | 3.92 |

The data shows that methyl carbamate was mostly converted to isopropyl carbamate (IPC) and not methylisopropyl carbonate. Low levels of di-isopropyl carbonate (DIPC) were detected in the autoclave. The collection vessel samples showed mostly IPA, some methanol and less than 1% DIPC.

EXAMPLE 40

This is a repeat of Example 39, except that the autoclave was operated at 140° C. and 75 psig ($5.171 \times 10^5$ N/m$^2$). Also, the 20 liter feed tank was charged with a mixture containing 65.21 wt. % IPA and 34.78 wt. % methanol. The results are represented in Tables 22 and 23.

TABLE 22

| Time | Autoclave, Wt. % | | | |
|---|---|---|---|---|
| Hours | MC | IPC | DIPC | MIPC |
| 0.66 | 20.27 | 13.97 | | 0 |
| 1.16 | 19.19 | 13.89 | | 0 |
| 2.08 | 17.19 | 13.4 | | 0 |
| 3 | 16.62 | 13.11 | | 0 |
| 4.5 | 15.44 | 12.77 | | 0.4 |
| 6 | 14.66 | 12.22 | | 0.45 |
| 7.5 | 13.76 | 11.68 | | 0.46 |
| 9.17 | 13.22 | 11.2 | | 0.46 |
| 13.75 | 11.52 | 10.2 | 0 | 0.4 |
| 22.75 | 9.59 | 8.09 | 0 | 0.44 |
| 24.92 | 8.72 | 7.31 | 0 | 0.38 |
| 25.25 | 8.47 | 7.54 | 0.28 | 0.44 |
| 26.42 | 7.9 | 6.65 | 0.3 | 0.46 |
| 27.75 | 7.48 | 6.43 | 0.33 | 0.52 |

TABLE 23

| Time Hours | % MIPC in Overhead | Wt. % DMC in Overhead |
|---|---|---|
| 1.33 | 0 | 0 |
| 2.16 | 0 | 0.13 |
| 4.16 | 0.19 | 0.2 |
| 5.58 | 0.23 | 0.23 |
| 7.08 | 0.22 | 0.22 |
| 8.75 | 0.24 | 0.24 |
| 13.33 | 0.22 | 0.22 |
| 23.33 | 0.2 | 0.21 |
| 25 | 0.21 | 0.18 |
| 26.5 | 0.2 | 0.19 |

The results show equal amounts of methylisopropyl carbamate (MIPC) and DMC in the overhead. The reactor contained IPC and methyl carbamate in addition to small amounts of DIPC and MIPC. This example illustrates that MIPC can be made by reacting methyl carbamate with a mixture of IPA and methanol.

EXAMPLE 41

This is a repeat of Example 39, except that the autoclave was operated at 154° C. and 121 psig ($8.343 \times 10^5$ N/m$^2$) and the 20 liter feed tank was charged with a mixture containing 84.91 wt. % IPA and 15.09 wt. % methanol. The results are summarized in Tables 24 and 25.

TABLE 24

| Time | Autoclave, Wt. % | | | | |
|---|---|---|---|---|---|
| Hours | MC | IPC | DIPC | MIPC | DMC |
| 0.17 | 25.87 | 10.98 | 0 | 0 | 0 |
| 0.33 | 21.08 | 13.76 | 0 | 0 | 0 |
| 0.5 | 18.17 | 14.64 | 0 | 0 | 0 |
| 0.75 | 16.97 | 14.34 | 0 | 0.37 | 0 |
| 1.08 | 16.23 | 16.6 | 0.52 | 0.87 | 0.45 |
| 1.67 | 13.54 | 18.15 | 1.32 | 1.64 | 0.51 |
| 2.5 | 10.14 | 19.59 | 2.91 | 2.56 | 0.49 |
| 3.5 | 7.94 | 20.25 | 4.4 | 3.1 | 0.46 |
| 4.5 | 6.9 | 19.94 | 6.24 | 3.47 | 0.44 |
| 5.42 | 6.16 | 19.05 | 6.9 | 3.62 | 0.43 |
| 6.42 | 5.73 | 17.84 | 7.47 | 3.7 | 0.41 |
| 8.75 | 4.72 | 14.57 | 7.53 | 3.61 | 0.34 |
| 13 | 3.61 | 10.33 | 6.28 | 3.01 | 0 |
| 23.5 | 1.63 | 4.01 | 2.44 | 1.21 | 0 |
| 24.92 | 1.38 | 3.43 | 2.17 | 1.05 | 0 |
| 26.62 | 1.21 | 3.04 | 1.85 | 0.89 | 0 |
| 28 | 1.12 | 2.96 | 1.83 | 0.85 | 0 |

TABLE 25

| Time | Overhead Vessel Wt. % | | |
|---|---|---|---|
| Hours | MIPC | DMC | DIPC |
| 1.25 | 0.29 | 0.31 | 0 |
| 2.58 | 0.6 | 0.5 | 0.2 |
| 4.58 | 1.1 | 0.63 | 0.59 |
| 5.5 | 1.41 | 0.6 | 1.02 |
| 6.5 | 1.46 | 0.57 | 1.12 |
| 8.92 | 1.44 | 0.51 | 1.15 |
| 14.25 | 1.22 | 0.42 | 0.98 |
| 23.58 | 0.69 | 0.24 | 0.56 |
| 24.92 | 0.55 | 0.13 | 0.42 |
| 26.64 | 0.43 | 0 | 0.3 |
| 28 | 0.29 | 0 | 0.23 |

The results show that MIPC, DIPM and DMC are all present in the reactor, with MIPC having the highest concentration. These carbonates were also present in the reactor in addition to IPC and methyl carbamate. The results demonstrate that the selectivity to MIPC depends on the IPA to methanol ratio fed to the autoclave.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A catalyst having the general structure:

where $R_1$ is any alkyl or aryl group; and R' is any aliphatic, cycloaliphatic, araliphatic, arylcycloaliphatic, heterocyclic aliphatic, or non-aromatic heterocyclic monohydric group comprising from 1 to about 16 carbon atoms.

2. A catalyst having the general structure (II):

where $R_1$ is any alkyl or aryl group; and R' is any aliphatic, cycloaliphatic, araliphatic, arylcycloaliphatic, heterocyclic aliphatic, or non-aromatic heterocyclic monohydric group comprising from 1 to about 16 carbon atoms.

3. The catalyst according to claim 1 wherein said catalyst is formed by reacting dialkyl dialkoxy tin (IV) with alkyl carbamate.

4. The catalyst according to claim 2 wherein said catalyst is formed using the following steps:

reacting dialkyl tin oxide with dialkyl carbonate, thereby forming tetraalkyl dialkoxydistannoxane; and reacting said tetraalkyl dialkoxydistannoxane with alkyl carbamate.

* * * * *